United States Patent
Duan et al.

(10) Patent No.: US 7,263,246 B1
(45) Date of Patent: Aug. 28, 2007

(54) OXYGEN DETECTION USING EVANESCENT FIELDS

(75) Inventors: Yixiang Duan, Los Alamos, NM (US); Weenqing Cao, Los Alamos, NM (US)

(73) Assignee: United States of America Department of Energy, Washington, DC (US)

( * ) Notice: Subject to any disclaimer, the term of this patent is extended or adjusted under 35 U.S.C. 154(b) by 0 days.

(21) Appl. No.: 11/357,154

(22) Filed: Feb. 21, 2006

(51) Int. Cl.
*G02B 6/00* (2006.01)
*G02B 6/42* (2006.01)

(52) U.S. Cl. .......................... 385/12; 385/30
(58) Field of Classification Search ................. None
See application file for complete search history.

(56) References Cited

U.S. PATENT DOCUMENTS 4,945,230 A * 7/1990 Saaski et al. .......... 250/227.21
5,043,285 A * 8/1991 Surgi .......................... 436/136
2004/0021100 A1* 2/2004 Gouzman et al. ........... 250/573

* cited by examiner

Primary Examiner—Tina M. Wong
(74) *Attorney, Agent, or Firm*—Thomas S. O'Dwyer; James C. Durkis; Paul A. Gottlieb

(57) ABSTRACT

An apparatus and method for the detection of oxygen using optical fiber based evanescent light absorption. Methylene blue was immobilized using a sol-gel process on a portion of the exterior surface of an optical fiber for which the cladding has been removed, thereby forming an optical oxygen sensor. When light is directed through the optical fiber, transmitted light intensity varies as a result of changes in the absorption of evanescent light by the methylene blue in response to the oxygen concentration to which the sensor is exposed. The sensor was found to have a linear response to oxygen concentration on a semi-logarithmic scale within the oxygen concentration range between 0.6% and 20.9%, a response time and a recovery time of about 3 s, ant to exhibit good reversibility and repeatability. An increase in temperature from 21° C. to 35° C. does not affect the net absorption of the sensor.

20 Claims, 7 Drawing Sheets

OXYGEN DETECTION USING EVANESCENT FIELDS

STATEMENT REGARDING FEDERAL RIGHTS

This invention was made with government support under Contract No. W-7405-ENG-36 awarded by the U.S. Department of Energy to The Regents of the University of California. The government has certain rights in the invention.

FIELD OF THE INVENTION

The present invention relates generally to detection of oxygen and, more particularly, to the detection of gaseous oxygen using absorption of evanescent radiation.

BACKGROUND OF THE INVENTION

Gaseous oxygen monitoring systems are useful for monitoring combustion, waste gases, atmospheric oxygen concentration, and chemical processes, as examples. To meet these requirements, a variety of methods for gaseous oxygen detection have been explored and developed. Significant attention has been given to the development of optical fiber based chemical sensors (OFCSs) for oxygen sensing [See, e.g., C. H. Jeong et al., "Application of the channel optical waveguide prepared by ion exchange method to the preparation and characterization of an optical oxygen gas sensor", Sens. Actuators B 105 (2005), pp. 214-218; B. J. Basu et al., "Optical oxygen sensor coating based on the fluorescence quenching of a new pyrene derivative", Sens. Actuators B 104 (2005), pp. 15-22; Y. Fujiwara, et al., "Novel optical oxygen sensing material: 1-pyrenedecanoic acid and perfluorodecanoic acid chemisorbed onto anodic oxidized aluminum plate", Sens. Actuators B 99 (2004), pp. 130-133; D. L. Plata et al. in "Aerogel-platform optical sensors for oxygen gas", J. Non-Cryst. Solids 350 (2004), pp. 326-335; Y. Fujiwara, et al., "Optimising oxygen-sensitivity of optical sensor using pyrene carboxylic acid by myristic acid co-chemisorption onto anodic oxidized aluminium plate", Talanta 62 (2004), pp. 655-660; P. A. S. Jorge et al., "Optical temperature measurement configuration for fluorescence based oxygen sensors", Proceedings of SPIE—The International Society for Optical Engineering; vol. 5502 (2004), pp. 279-282; N. Leventis et al., "Synthesis and Characterization of Ru (II) Tris (1,10-phenanthroline)—Electron Acceptor Dyads Incorporating the 4-Benzoyl-N-methylpyridinium Cation or N-Benzyl-N-methyl Viologen. Improving the Dynamic Range, Sensitivity, and Response Time of Sol-Gel-Based Optical Oxygen Sensors", Chem. Mater. 2004, 16, pp. 1493-1506; O. S. Wolfbeis, "Fiber-optic chemical sensors and biosensors" Anal. Chem. 2004, 76, pp. 3269-3284; Y. Amao, "Probes and polymers for optical sensing of oxygen" Microchim. Acta 143 (2003), pp. 1-12; D. Jiang et al., "Optical fiber oxygen sensor based on fluorescence quenching", Acta Optica Sinica 23 (2003), pp. 381-384; K. Eaton et al., "Effect of humidity on the response characteristics of luminescent PtOEP thin film optical oxygen sensors", Sens. Actuators B, 82 (2002), pp. 94-104; K. Mitsubayashi et al., "Bio-optical gas-sensor (sniffer device) with a fiber optic oxygen sensor" in: Conference on Optoelectronic and Microelectron Materials and Devices, Sydney, NSW, Australia Dec. 11-13, 2002, p. 213-16; M. Kölling et al., "A simple plastic fiber based optode array for the in-situ measurement of ground air oxygen concentrations" in: Proceedings of SPIE—The International Society for Optical Engineering; vol. 4576 (2002), pp. 75-86; A. A. Kazemi et al., "Fiber optic oxygen sensor detection system for aerospace applications" in: Proceedings of the SPIE—The International Society for Optical Engineering; vol. 4204 (2001), pp. 131-138; G. Vishnoi et al., "A new plastic optical fiber sensor for oxygen based on fluorescence enhancement" Opt. Rev. 5, No. 1 (1998), pp. 13-15; A. Mills, "Controlling the sensitivity of optical oxygen sensors", Sens. Actuators B 51 (1998), pp. 60-68; and L. Xin et al., "Luminescence quenching in polymer/filler nanocomposite films used in oxygen sensors" Chem. Mater. 13 (2001), pp. 3449-3463.]. Optical fiber based chemical sensors have small size and flexibility which render these sensors useful for in situ and in vivo sensing. Since the optical fibers used for OFCSs can transmit chemically-encoded information between a remote sample and a spectrometer, the optical fiber based sensors are suitable for in situ monitoring of environmental hazards in hostile or not readily accessible environments. In addition, optical fibers are relatively insensitive to noise from radioactivity and electric fields, and signals acquired with optical fibers are less affected by environmental interferences than those transmitted through electrical wires. Optical fibers can also transmit a high density of information. Wavelength, polarization, and phase information enhances both the quality and quantity of chemical information obtained by OFCSs.

For the past few years, optical sensors for oxygen sensing have been based on dynamic quenching of luminescence generated in chemical or photo reactions. The principle of photo-luminescent or photoexcited state quenching of organic dyes by oxygen is described in Y. Amao, supra; A. Mills, supra; and R. Ramamoorthy et al., "Oxygen sensors: materials, methods, designs and applications" J. Mater. Sci. 38 (2003), pp. 4271-4282, as examples. Typically, this type of optical oxygen sensor is composed of organic dyes, such as polycyclic aromatic hydrocarbons (pyrene, pyrene derivatives, etc.), transition metal complexes ($Ru^{2+}$, $Os^{2+}$, $Ir^{3+}$, etc.), metalloporphyrins ($Pt^{2+}$, $Pd^{2+}$, $Zn^{2+}$ etc.) and fullerene ($C_{60}$ and $C_{70}$), immobilized in oxygen-permeable polymer films [See, e.g., Y. Amao, supra.]. The quenching of the luminescence may be characterized by the Stern-Volmer equation, and several oxygen sensors having various sensitivities have been developed using this principle [See, e.g., A. Mills, supra.]. However, the Stern-Volmer quenching constant is sensitive to the oxygen diffusion coefficient for the encapsulating medium [See, e.g., A. Mills, supra.]; therefore, it is difficult to control the repeatability and uniformity of such sensors.

Accordingly, it is an object of the present invention to provide an apparatus and method for detecting oxygen having good repeatability and response time.

Additional objects, advantages and novel features of the invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus for detecting gaseous oxygen includes: an optical fiber having an exterior cladding, a first end and a second end, a portion of the cladding between the first end and the second end being removed from the optical fiber; a coating disposed on the portion of the surface of the optical fiber for which the cladding has been removed, the coating including methylene blue, whereby the methylene blue supports an intensity of evanescent radiation from the optical fiber responsive to the level of oxidation of the methylene blue; means for exposing the coating to a gas containing said gaseous oxygen; a light source for generating wavelengths of light in part absorbed by the methylene blue in accordance with the level of oxidation thereof; means for directing the selected wavelengths of light into the first end of the optical fiber; and means for detecting the intensity of selected wavelengths of light exiting the second end of the optical fiber, whereby the change in intensity of the evanescent radiation dependant on the concentration of gaseous oxygen affects the detected intensity of selected wavelengths exiting the second end of the optical fiber.

In another aspect of the present invention, in accordance with its objects and purposes, the method for detecting gaseous oxygen includes the steps of: coating the surface of an optical fiber for which the cladding thereof has been partially removed with a coating including methylene blue, whereby the methylene blue supports an intensity of evanescent radiation from the optical fiber responsive to the level of oxidation of the methylene blue; exposing the coating to a gas containing the gaseous oxygen; generating wavelengths of light in part absorbed by the methylene blue in accordance with the level of oxidation thereof; directing the selected wavelengths of light into one end of the optical fiber; and detecting the intensity of selected wavelengths of light exiting the other end of the optical fiber, whereby the change in intensity of the evanescent radiation dependant on the concentration of gaseous oxygen affects the detected intensity of selected wavelengths exiting the end of the optical fiber.

Benefits and advantages of the present invention include, but are not limited to, a sensor for the detection of oxygen which exhibits good reversibility, and repeatability, and temperature independence with baseline correction.

BRIEF DESCRIPTION OF THE DRAWING

The accompanying drawings, which are incorporated in and form a part of the specification, illustrate several embodiments of the present invention and, together with the description, serve to explain the principles of the invention.

FIG. 6A is a graph of the reversibility of response for the sensor of the present invention, while

DETAILED DESCRIPTION

Briefly, the present invention includes an apparatus and method for detecting gaseous oxygen using oxygen-induced changes in the absorption of the evanescent field resulting from color changes in the methylene blue cladding of an optical fiber. The dye methylene blue changes color depending upon its state of oxidation or reduction. This color change is known to be closely related to the concentration of oxygen in contact with the dye, and may be used as an oxidation/reduction indicator. Methylene blue can be immobilized as a partial replacement cladding on an optical fiber using a sol-gel process. The evanescent field interacts with methylene blue coating in the replacement cladding of the optical fiber [See, e.g., Wenqing Cao and Yixiang Duan, "Optical fiber-based evanescent ammonia sensor" Sens. Actuators B 110 (2005), pp. 252-259.], producing the sensor of the present invention.

When a beam of light propagates in the core of an optical fiber, the electromagnetic field does not abruptly fall to zero at the interface between core and cladding. Rather, the overlap of the incoming beam and the internally reflected beam generates a field that penetrates into the medium next to the core. This electromagnetic field, which tails off in intensity, but does not propagate into the second medium, is called the evanescent field. Its intensity decays exponentially with the distance perpendicular to the interface. The absorption of this evanescent wave along optical fiber resulting from the interaction of the evanescent field with the methylene blue modulates the light intensity in the core of the fiber and can be utilized to detect oxygen concentration.

The tested dynamic sensing range of the present invention of between 0.6% and 20.9% renders the subject oxygen sensor suitable for detecting oxygen deficiency in human-occupied enclosures. For example, oxygen levels in enclosed spaces can be depleted when liquid nitrogen boils, frozen carbon dioxide sublimes, or argon, nitrogen or other process gases purge. Further, in submarines, space vehicles, and mines, oxygen can be consumed and fall to dangerously low values as a result of failure of oxygen generating or circulating equipment. Fresh air generally contains about 20.9% oxygen. Environments for which the concentration of oxygen falls to below 19.5% have been determined by the Occupational Safety and Health Administration (OSHA) to be oxygen deficient.

Figure 1:
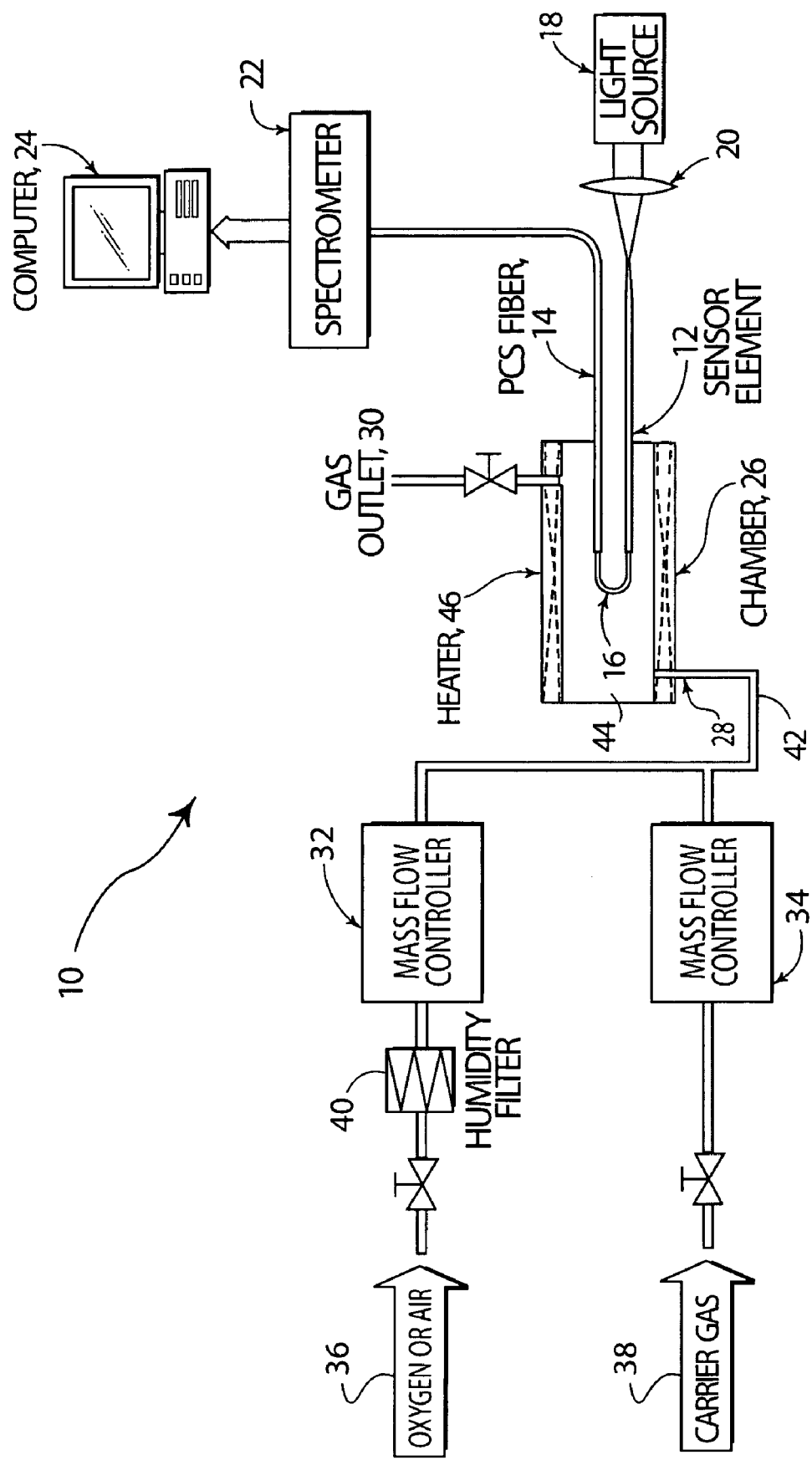
FIG. 1 is a schematic representation of an embodiment of the apparatus of the present invention for oxygen detection using optical fiber-based evanescence.

Reference will now be made in detail to the present preferred embodiments of the present invention, examples of which are illustrated in the accompanying drawings. Similar or identical structure is labeled using identical callouts. Turning now to the FIGURES, FIG. 1 is a schematic representation of an embodiment of the apparatus, 10, of the present invention for oxygen detection using optical fiber-based evanescence. Sensor element, 12, includes optical fiber, 14, from which a portion of the cladding was removed, 16, and the optical fiber coated with methylene blue fixed in a sol gel, as will be described hereinbelow in the EXAMPLE. Optical fiber 14 was formed into a U-shape in the region of the removed cladding to improve exposure to the gas under investigation. Other shapes, such as a coil, as an example, which increase the area of the optical fiber coated with methylene blue exposed to the oxygen-containing gas would be advantageous. Tungsten halogen light source, 18, was coupled into optical fiber 14 through one end thereof by means of lens, 20. Fiber optic spectrometer, 22, adapted to receive signals from the other end of optical fiber 14, was employed to measure the absorption properties of the oxygen gas. The output from spectrometer 22 was directed to computer, 24 for analysis and recording.

Sensor element 12 was placed in a quartz cylindrical chamber, 26, having an inner diameter of 2.5 cm and a wall thickness of 0.2 cm, and constructed using endcaps and airtight penetrations. Clearly, chambers having other configurations, dimensions and other materials of construction may be employed as dictated by the intended environment of use of sensor 12. Gas inlet, 28, and gas outlet, 30, were positioned at opposite ends of chamber 26. The downside port was used as the gas inlet and the upside port as the outlet for the oxygen-containing sample. Other configurations may be used as well. Oxygen mass flow rate and oxygen concentration in a selected diluent were controlled for calibration purposes using mass flow controllers, 32 and 34, respectively. Ultra high purity compressed oxygen (99.99%), 36, and nitrogen (99.9995%), 38, were used as the oxygen source and carrier/diluent gas, respectively.

Compressed dry air (CDA) was also employed to characterize the properties of the oxygen sensor. Humidity filter, 40, was used to dry the CDA when used. Gas mixing occurs in part in delivery tube, 42, and in the interior, 44, of chamber 26.

Chamber 26 was wrapped with an electrical resistance belt heater, 46, for temperature control and temperature dependence investigation. The temperature of the interior of chamber 26 was calibrated and monitored using a digital thermometer, not shown in FIG. 1. In actual operation as an oxygen sensor, oxygen supply 36 of apparatus 10 would be replaced by a source of the gas to be tested which would either be compressed and forced into chamber 26 through inlet 28, or introduced thereto by providing a vacuum at outlet 30, not shown in FIG. 1.

Having generally described the present apparatus, the operation thereof is described in the following EXAMPLE.

EXAMPLE

A. Preparation of the Optical Fiber Sensor

Both ends of a 50 cm long plastic clad silica (PCS) multi-mode optical fiber 14 having a core diameter of 600 µm were polished using 2000-grit and 3 µm polishing film. The plastic jacket of the PCS fiber was removed from the central portion of the fiber along a 6 cm length by chemical etching by immersing the fiber into a 50% HF solution for 10 min. Since evanescent radiation represents a small fraction of the light power introduced into the fiber, the present optical fiber oxygen sensor was constructed with a U-shaped bend to enhance absorbance. As stated hereinabove, other configuration may be used. The diameter of the semicircle portion of the U-shape structure was about 1.5 cm. Other diameters may be used, except that care must be taken to avoid breaking the optical fiber as a result of too sharp of a bend.

B. Sol-Gel Film Fabrication:

Sol-Gel is an optically transparent glasslike material formed by hydrolysis and polymerization of metal alkoxides or metal organic compounds at low temperatures, having a porous matrix with interconnected pores formed by a three-dimensional network of $SiO_2$. Tetraethyl orthosilicate (TEOS) was used as the precursor for the sol preparation, since the refractive index of the generated porous silica film is smaller than that of the fiber core. Methylene blue (Basic Blue 9, $C_{16}H_{18}ClN_3S.3H_2O$) was the oxygen-sensitive dye used in the present apparatus. A magnetic stirrer was used to mix the sol-gel reagents as follows:

1. 10 ml of deionized water was acidified using 37% HCl to pH=1;
2. 45 ml of TEOS was mixed with 55 ml of ethanol for 20 min.;
3. 10 ml of the acidified water was added and mixing continued for 1 h;
4. 10 ml of ethanol containing 10 mg methylene blue was added, with stirring continued for 1 h;
5. The surface of the PCS fiber having the cladding removed was treated with 30% $HNO_3$ for 10 min. to activate the OH groups at the core surface;
6. The treated fiber was coated using a dip coating procedure.
7. The coated fiber was dried overnight in an oven at 75° C. and stored at ambient conditions away from direct sunlight for greater than about one week prior to characterization. This storage period was found to permit adequate post-fabrication structural evolution of the silica matrix to occur [See, e.g., C McDonagh et al., "Characterisation of sol-gel-derived silica films" J. Non-Cryst. Solids 194 (1996), pp. 72-77.].

No difference was observed for the detection of ultra high purity compressed oxygen and dried CDA with equal oxygen concentrations. When the nitrogen diluent/carrier gas was replaced by argon, there was also no observed effect. In order to best reproduce the conditions for detecting oxygen in the field, the following results were obtained using dried CDA diluted by nitrogen.

Figure 2:
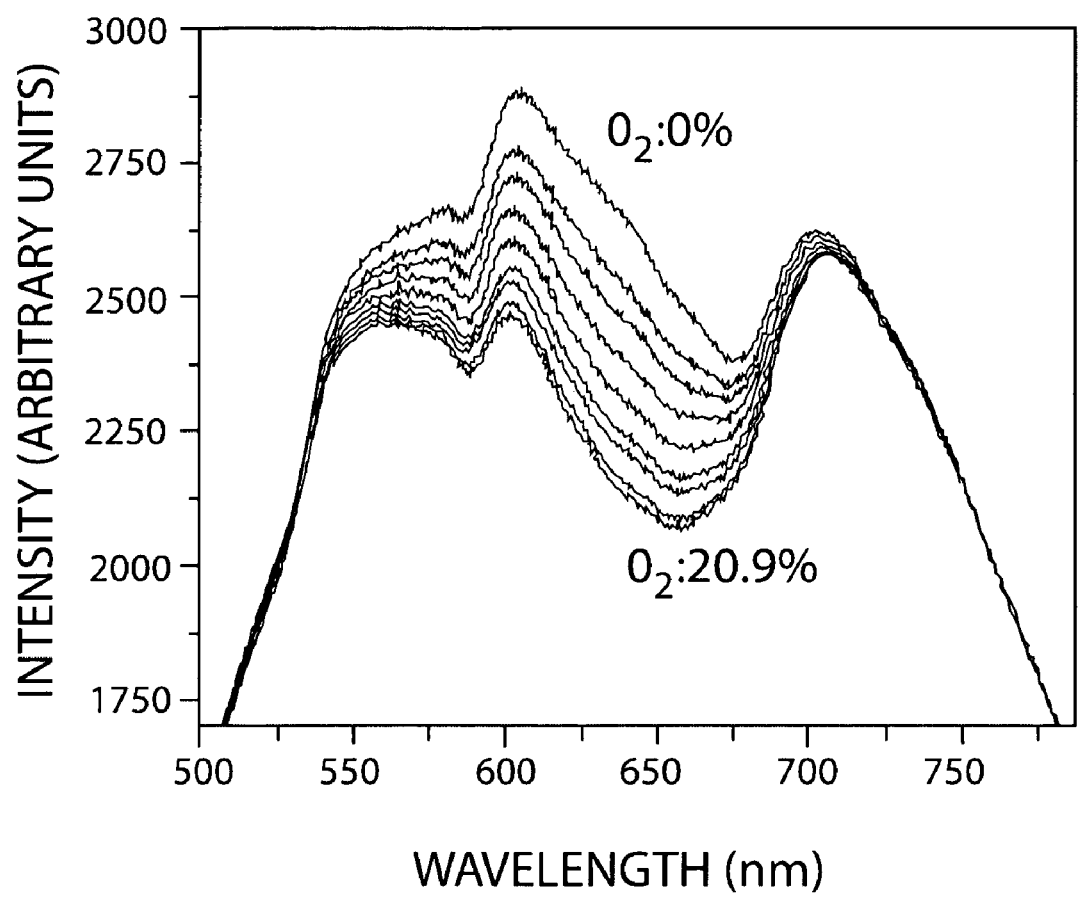
FIG. 2 shows spectra obtained at the oxygen concentrations of 0%, 0.6%, 1.0%, 2.0%, 4.0%, 7.0%, 10.0%, 15.0%, and 20.0%.

Methylene blue changes color when exposed to different concentrations of oxygen, resulting in different evanescent wave absorptions of the radiation from the tungsten halogen light source. FIG. 2 shows observed spectra for different concentrations of oxygen. The oxygen concentration was increased by volume in the steps: 0%, 0.6%, 1.0%, 2.0%, 4.0%, 7.0%, 10.0%, 15.0%, and 20.0%. It is observed that the evanescent wave absorption increases with the increase of oxygen concentration. In order to generate the net evanescent wave absorption as a function of oxygen concentration, a background spectrum obtained with only nitrogen carrier gas was subtracted from sample spectra containing known concentrations of oxygen.

Figure 3:
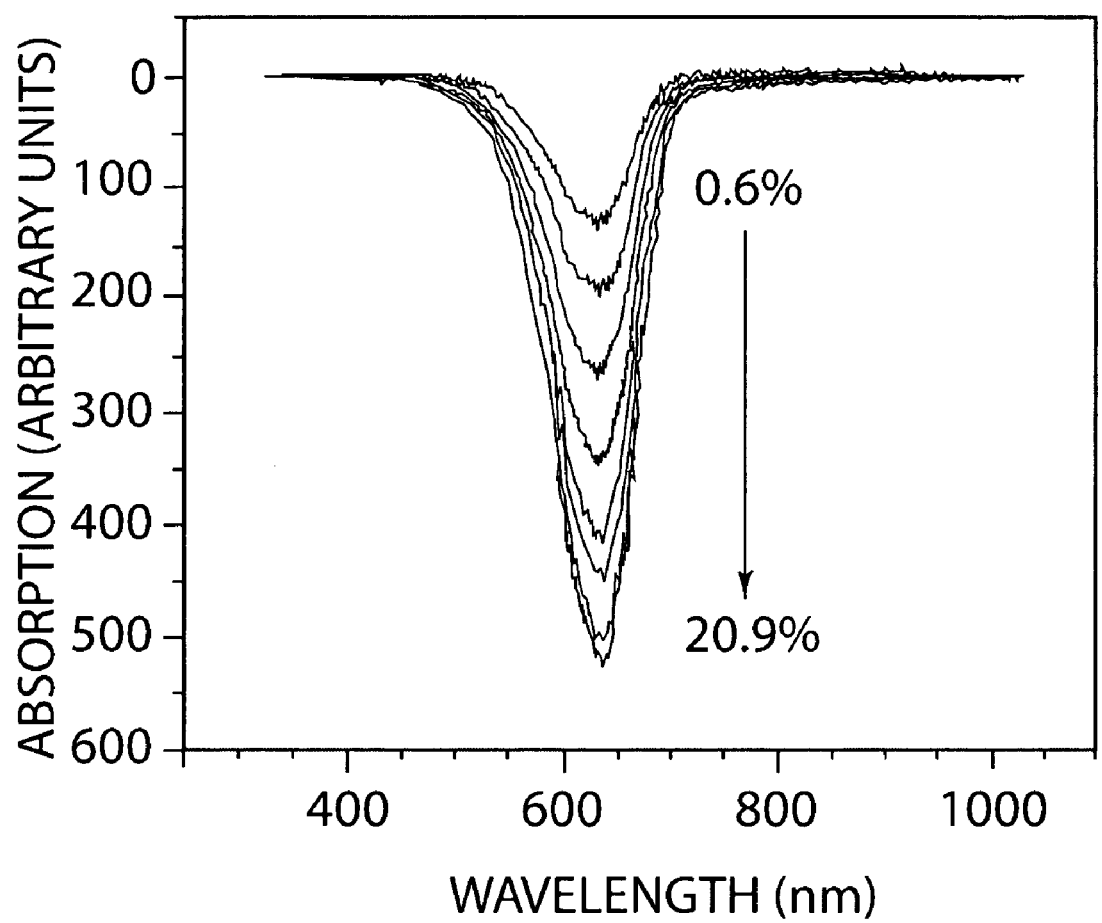
FIG. 3 shows evanescent wave absorption spectra for the oxygen concentrations of 0%, 0.6%, 1.0%, 2.0%, 4.0%, 7.0%, 10.0%, 15.0%, and 20.0%, with background having been subtracted.

FIG. 3 shows the net absorption spectra obtained through background subtraction for oxygen concentrations between 0.6% and 20.9%. The total mass flow rate of carrier gas and sample gas was set at 1000 sccm (standard cubic centimeter per minute). Absorption peaks for various concentrations of oxygen were recorded together for comparison purposes. FIG. 3 shows that the absorption increases with increasing oxygen concentration. A maximum of the absorption was identified for the oxygen concentrations tested to lie at 636 nm.

Figure 4:
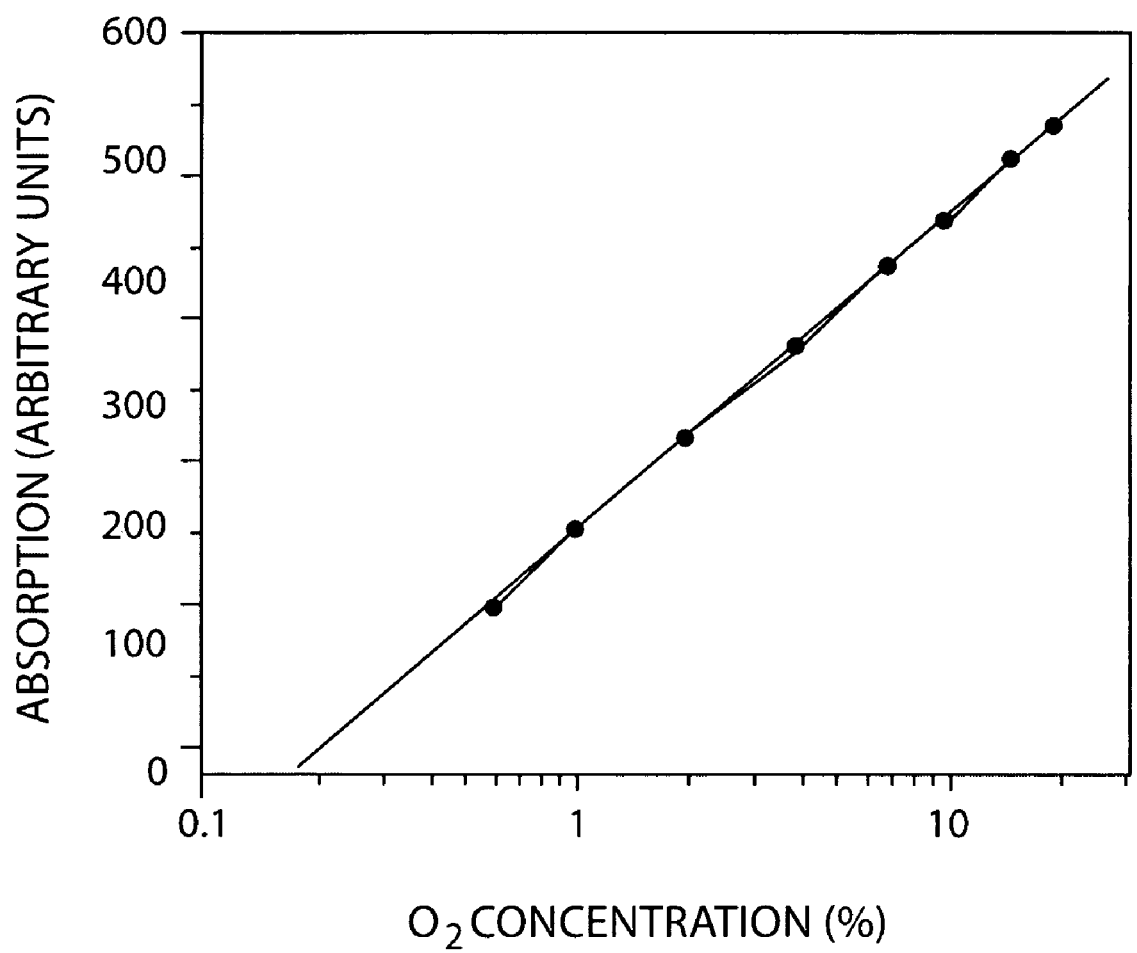
FIG. 4 is a calibration curve for the evanescent wave absorption as a function of oxygen concentration.

FIG. 4 shows the linear logarithmic variation of absorption as a function of oxygen gas concentration within the range of concentration between 0.6% and 20.9% at a wavelength of 636 nm. The test range was limited by the dilution capability of the mass flow controllers, the lowest obtainable oxygen concentration being about 0.6%. However, based on FIG. 4, a detection limit of about 0.16% for the present oxygen sensor can be estimated by extending the line of best fit to the X-axis. Since oxygen concentrations less than 19.5% are considered to be oxygen deficient, the linear dynamic range of the present oxygen sensor is suitable for monitoring oxygen deficiency.

Figure 5:
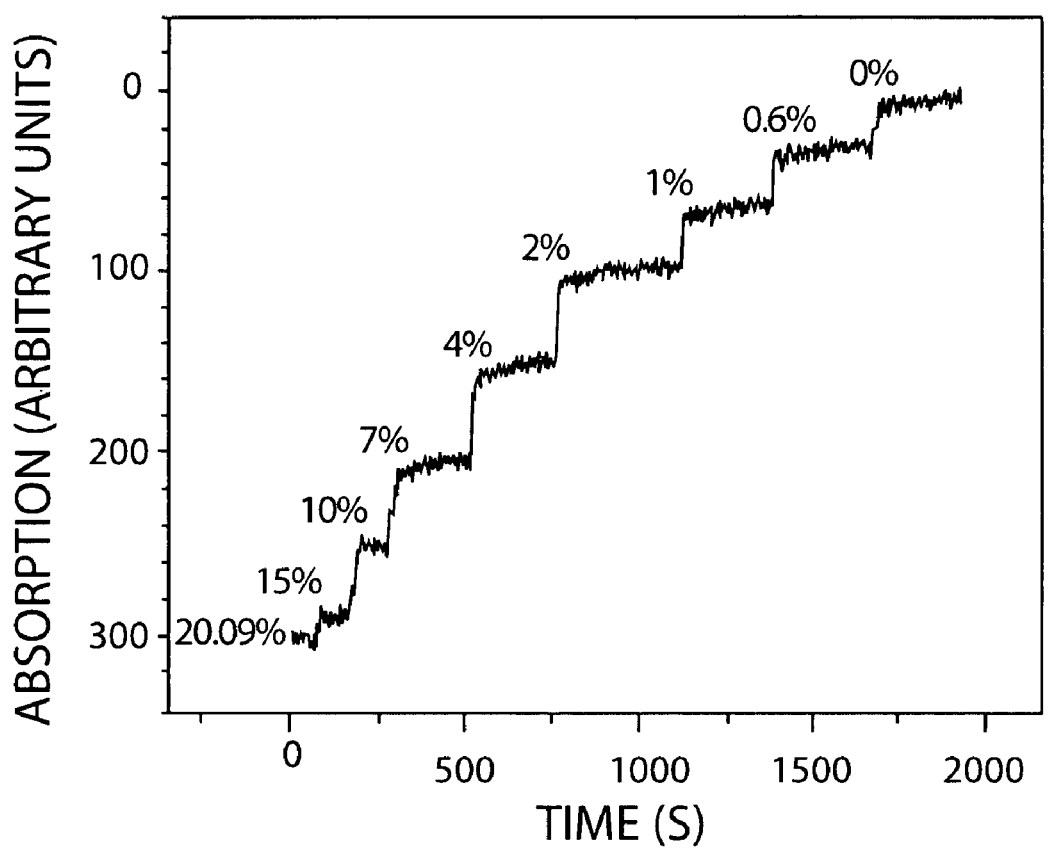
FIG. 5 is a graph of the evanescent wave absorption as a function of the time dependence of the oxygen concentration at 636 nm.

FIG. 5 shows the variation of the absorption as a function of step-by-step variation of oxygen concentration from a concentration of 20.9% to a concentration of 0%. These absorption responses are similar to the results shown in FIG. 4 hereof.

Figure 6B:
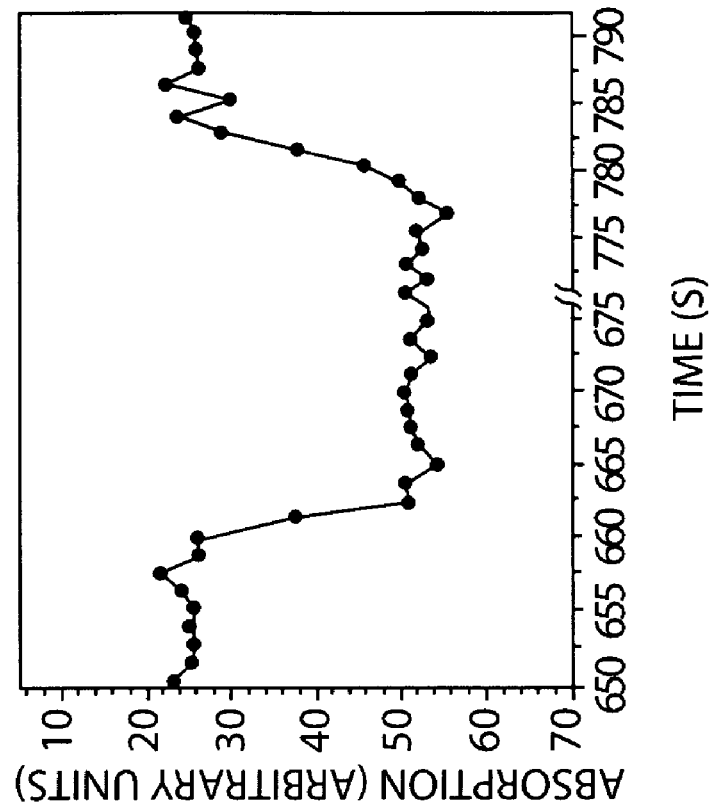
FIG. 6B illustrates the recovery time thereof.
Figure 6A:
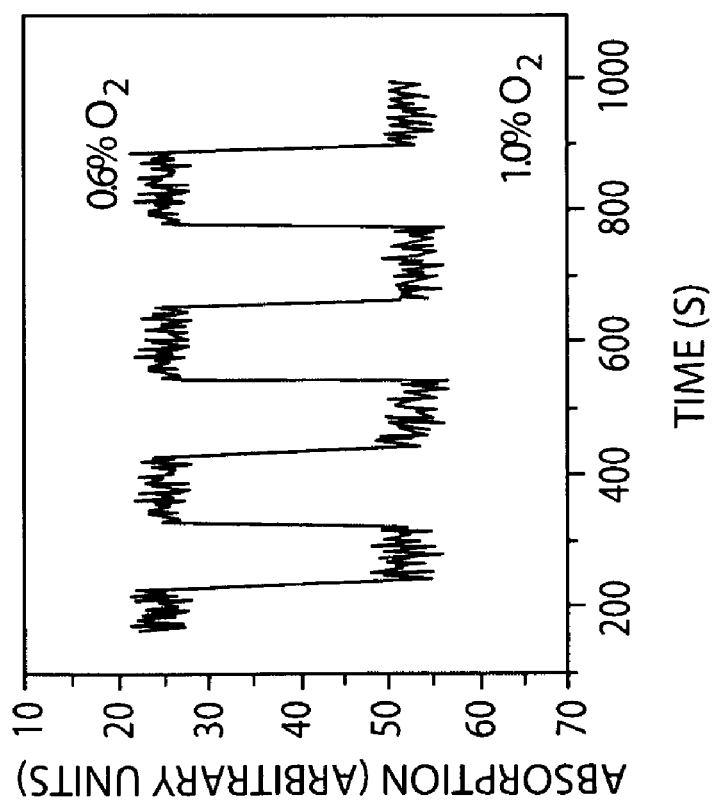

Reversibility, response time, and recovery time were investigated for the present oxygen sensor. The response of optical fiber sensor to 0.6% and 1.0% oxygen concentrations in nitrogen at a mass flow rate of 1000 sccm were measured. The absorption of evanescent radiation at 636 nm is plotted in FIG. 6A and FIG. 6B for these two oxygen concentrations, respectively. As shown in FIG. 6A, the present oxygen sensor exhibits good reversibility and repeatability.

In accordance with the definition of response time as determined by the interval between 10% and 90% of the stationary value [See, e.g., A. D'Amico et al., "Sensors parameters, sensors for domestic applications" Proceedings of the First European School on Sensors (ESS'94), Castro Marina, Lee, Italy, Sep. 12-17, 1994, pp. 3-13.], the response time of the present sensor shown in FIG. 6B hereof is approximately 3 s. Similarly, the recovery time is identified to be about 3 s as well. It is believed by the present inventors that the observed 3 s response time and the 3 s recovery time were limited by the time required to purge the volume of chamber 26. The actual response time and recovery time of the new sensor is likely to be shorter than 3 s, and shorter than that of currently available optical fiber based oxygen sensors [See, e.g., G. Vishnoi, supra, and B. D. MacCraith et al., "Sol-gel coatings for optical chemical sensors and biosensors," Sens. and Actuators B 29 (1995), pp. 51-57.]. If required, the response time of the present sensor could be further reduced by improving the design of the absorption cell, or by using an optical fiber with a thinner silicone cladding [See, e.g., W. Cao and Y. Duan, supra.].

It is known that most dyes have temperature sensitive response characteristics. There is often a critical temperature above which dyes tend to cease their response and may irreversibly dissociate [See, e.g., B. Culshaw, "Optical fiber sensor technologies: opportunities and-perhaps-pitfalls," J. Lightwave Tech. 22 (2004), pp. 39-50.]. The sensing properties of the present oxygen sensor were measured at 21° C. (room temperature) and at 35° C. (elevated temperature). For each temperature, the oxygen concentration was changed from 0.0% to 0.6%, followed by a change between 0.6% and 1.0%. The intensities of the spectra at 636 nm for different oxygen concentrations and different temperatures were recorded.

Figure 7A:
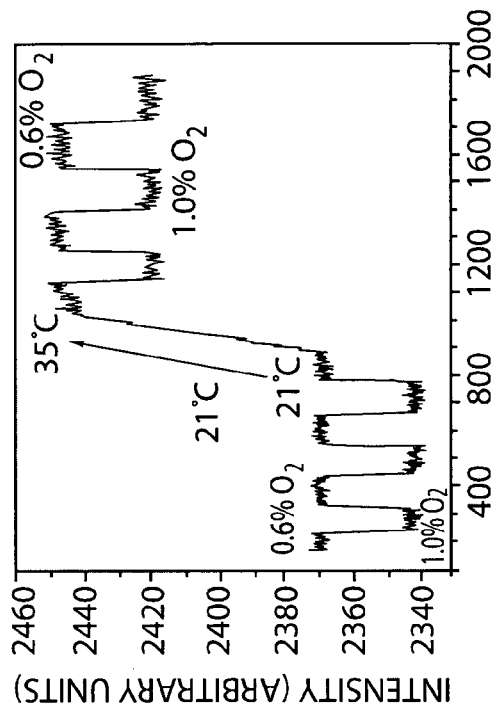
FIG. 7A is a graph of the effect of temperature on the intensity of the spectra detected by the present evanescent sensor at a fixed wavelength of 636 nm at 21° C. and 35° C. for two oxygen concentrations.
Figure 7B:
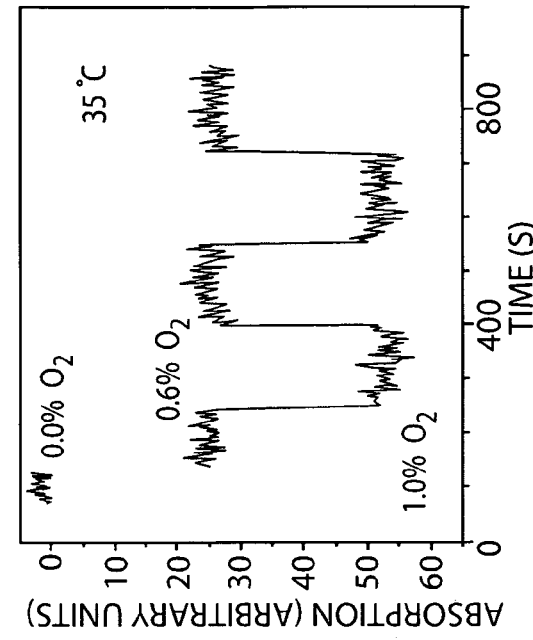
FIG. 7B is a graph of the measured absorption for two oxygen concentrations at 21° C.
Figure 7C:
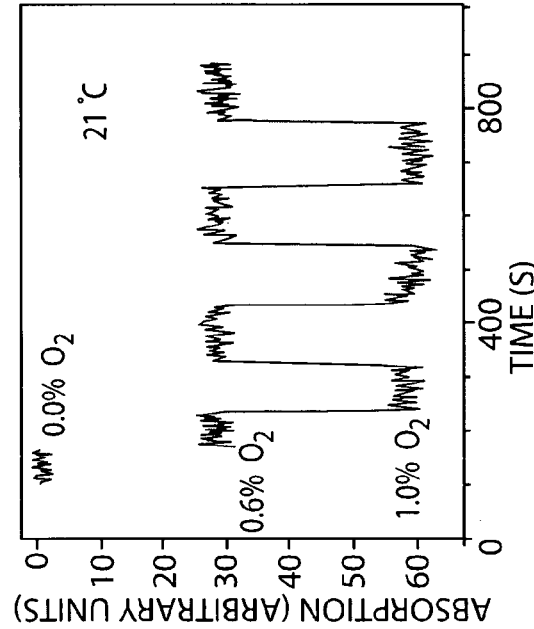
FIG. 7C is a graph of the measured absorption for two oxygen concentrations at 35° C.

FIG. 7A shows the variation of the intensity of the spectrum at 636 nm between 21° C. and 35° C.; to be observed is that the spectrum intensity increases with increasing temperature. Since the response of the sensor to oxygen is related to the evanescent field absorption rather than the intensity of the spectrum, the spectrum intensities for nitrogen (without added oxygen) at 21° C. and 35° C. were subtracted from the intensities from the corresponding intensities having oxygen concentrations of 0.6%, and 1.0%, to obtain the net absorptions for these samples at 21° C. and 35° C., respectively. This is illustrated in FIGS. 7B and 7C. By comparing the absorbances shown in FIGS. 7B and 7C, when the temperature increased from 21° C. to 35° C., the absorption values (in arbitrary units) for 0.6% and 1.0% are approximate 25 and 53, respectively, at both 21° C. and 35° C. Hence, a temperature increase shifts both the background and spectrum intensities, with the net absorption values from different oxygen samples remaining unchanged from 21° C. to 35° C.

The response time and recovery time also remained unchanged when the temperature was increased from 21° C. to 35° C., likely as a result of the fact that the sensor response and recovery are fast. Thus, the rate of chemical reaction involved in the sensing process is not dominated by temperature.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for detecting gaseous oxygen comprising in combination:
    (a) an optical fiber having an exterior cladding, a first end and a second end, a portion of the cladding between the first end and the second end being removed from said optical fiber;
    (b) a coating disposed on the portion of the surface of said optical fiber for which the cladding has been removed, said coating comprising methylene blue, whereby said methylene blue supports an intensity of evanescent radiation from said optical fiber responsive to the level of oxidation of said methylene blue;
    (c) means for exposing said coating to a gas containing said gaseous oxygen;
    (d) a light source for generating wavelengths of light in part absorbed by said methylene blue in accordance with the level of oxidation thereof;
    (e) means for directing the selected wavelengths of light into the first end of said optical fiber; and
    (f) means for detecting the intensity of selected wavelengths of light exiting the second end of said optical fiber; and
    (g) means for analyzing the intensity of the selected wavelengths of light detected to determine the change in intensity of the evanescent radiation which is dependent upon the concentration of exposed gaseous oxygen.

2. The apparatus of claim 1, wherein said coating comprises a sol gel.

3. The apparatus of claim 2, wherein said means for exposing said sol gel to said gaseous oxygen comprises an airtight chamber.

4. The apparatus of claim 3, wherein said chamber comprises a temperature controller, such that the temperature of said chamber can be maintained at a chosen value.

5. The apparatus of claim 1, further comprising means for removing water from the gas containing said oxygen before said oxygen contacts said coating.

6. The apparatus of claim 1, wherein said means for directing the selected wavelengths of light into the first end of said optical fiber comprises a lens.

7. The apparatus of claim 1, wherein said means for detecting the selected wavelengths of light exiting the second end of said fiber comprises a spectrometer.

8. The apparatus of claim 7, wherein the means for analyzing said spectrometer output is accomplished by directing such detection data to a computer for recording and comparison to background spectrum.

9. The apparatus of claim 1, wherein said wavelength generated by said light source comprises 636 nm.

10. The apparatus of claim 1, wherein said optical fiber comprises a plastic clad silica multi-mode optical fiber.

11. A method for detecting gaseous oxygen comprising the steps of:
   a. coating the surface of an optical fiber for which the cladding thereof has been partially removed with a coating comprising methylene blue, whereby the methylene blue supports an intensity of evanescent radiation from the optical fiber responsive to the level of oxidation of the methylene blue;
   b. exposing the coating to a gas containing said gaseous oxygen;
   c. generating wavelengths of light in part absorbed by the methylene blue in accordance with the level of oxidation thereof;
   d. directing the selected wavelengths of light into on end of the optical fiber; and
   e. detecting the intensity of selected wavelengths of light exiting the other end of the optical fiber; and
   f. analyzing the intensity of the selected wavelengths of light detected to determine the change in intensity of the evanescent radiation which is dependent upon the concentration of exposed gaseous oxygen.

12. The method of claim 11, wherein the coating comprises a sol gel support for the methylene blue.

13. The method of claim 12, wherein the sol gel is exposed to the gaseous oxygen in an airtight chamber.

14. The method of claim 13, further comprising the step of controlling the temperature of the airtight chamber.

15. The method of claim 13, further comprising the step of removing water from the gas containing the oxygen before the oxygen contacts the coating.

16. The method of claim 13, wherein said step of directing the selected wavelengths of light into the optical fiber is accomplished using a lens.

17. The method of claim 13, wherein said step of detecting the selected wavelengths of light exiting the fiber is accomplished using a spectrometer.

18. The method of claim 17, wherein the step of analyzing said spectrometer output is accomplished by directing such detection data to a computer for recording and comparison to background spectrum.

19. The method of claim 13, wherein light produced in said step of generating wavelengths of light comprises 636 nm.

20. The method of claim 13, wherein the optical fiber comprises a plastic clad silica multi-mode optical fiber.

\* \* \* \* \*